(12) United States Patent
Berg et al.

(10) Patent No.: US 9,067,899 B2
(45) Date of Patent: *Jun. 30, 2015

(54) PROCESS FOR PREPARING 1,2-BENZOISOTHIAZOLIN-3-ONES

(71) Applicants: Carsten Berg, Borre (DK); Sangita Singh, Surrey (GB); Ian Roger Marsh, Surrey (GB)

(72) Inventors: Carsten Berg, Borre (DK); Sangita Singh, Surrey (GB); Ian Roger Marsh, Surrey (GB)

(73) Assignee: TITAN CHEMICALS LIMITED, Tortola (VG)

( * ) Notice: Subject to any disclaimer, the term of this patent is extended or adjusted under 35 U.S.C. 154(b) by 23 days.

This patent is subject to a terminal disclaimer.

(21) Appl. No.: 13/868,297

(22) Filed: Apr. 23, 2013

(65) Prior Publication Data
US 2014/0316141 A1 Oct. 23, 2014

(51) Int. Cl.
C07D 275/04 (2006.01)

(52) U.S. Cl.
CPC .................................... *C07D 275/04* (2013.01)

(58) Field of Classification Search
USPC ........................................................ 548/209
See application file for complete search history.

(56) References Cited

U.S. PATENT DOCUMENTS

| 4,727,188 A | 2/1988 | Jaedicke |
| 8,476,452 B2 * | 7/2013 | Berg et al. ............... 548/209 |

FOREIGN PATENT DOCUMENTS

| CA | 1269985 | 6/1990 |
| JP | 06-345723 | 12/1994 |
| WO | 2013/060766 | 5/2013 |

OTHER PUBLICATIONS

V. Krasikova et al., "Preparation of . . . Catalysis Conditions", Chemistry of Heterocyclic Compounds, Feb. 11, 2013, pp. 1684-1690, XP055118595.
Fei Wang et al., "Concise Approach . . . Thiocyanate in Water", The Journal of Organic Chemistry, vo. 77, No. 8, Apr. 20, 2012, pp. 4148-4151, XP055118592.
Peter Barnfield et al., "Conversion of . . . o-Aminobenzenesulphonic Acids", J. Chem. Soc. Perkin Trans, 1988, XP055118501.
Siegemund A. et al., "1,2-Benzisothiazol-3(2H)-Ones . . . Biological Activity", Sulfur Reports, Harwood Academic Publishers, Cur, Ch, vol. 23, No. 3, 2002, pp. 279-319, XP009165054.

* cited by examiner

*Primary Examiner* — Laura L. Stockton
(74) *Attorney, Agent, or Firm* — Clark & Brody

(57) ABSTRACT

Sodium sulfide hydrate is at least partially dehydrated by heating with N-methyl 2-pyrrolidone. 2-Chlorobenzamide is added to the mixture which is heated further. The mixture is cooled and treated with aqueous hydrogen peroxide to give the sodium salt of 1,2-benzisothiazolin-3-one in good yield. Acidification if desired gives rise to the free 1,2-benzisothiazolin-3-one.

6 Claims, No Drawings

PROCESS FOR PREPARING 1,2-BENZOISOTHIAZOLIN-3-ONES

This invention relates to processes for making 1,2-benzisothiazolin-3-ones. More especially but not exclusively the invention relates to methods for making N-substituted 1,2-benzisothiazolin-3-ones. 1,2-benzisothiazolin-3-one sometimes referred to as BIT is known as a biocide. 2-methyl-1,2-benzoisothiazolin-3-one, CAS #2527-66-4, sometimes referred to as Me-BIT is a biocide and fungicide. Other N-substituted 1,2 benzoisothiazolin-3-ones have biocidal and or fungicidal properties.

CA 1 269 985 and U.S. Pat. No. 4,727,188 describe processes for preparing 1,2-benzisothiazolin-3-ones. In a first step and as described in U.S. Pat. No. 4,727,188 anthranilamide is nitrosated by reaction with a nitrite (ie nitrate III) followed by reaction with sulfur dioxide to give 2,2'-dithiodibenzamide. It is well known that nitrosation is implicated in the formation of nitrosoamines which can be a health hazard and the reaction is in any event difficult to perform on an industrial scale. As an alternative to this reaction 2,2'-dithiodibenzamides can be made from the corresponding acyl chloride but according to U.S. Pat. No. 4,727,188 this reaction is difficult to perform.

The ensuing 2,2' dithiodibenzamide is then subjected to oxidative ring closure. The reaction is performed in alkaline conditions in the presence of oxygen or an oxygen donor such as a peracid in CA 1 269 985.

The invention seeks to provide alternative processes for preparing 1,2-benzisothiazolin-3-ones.

A process for preparing a compound of Formula I

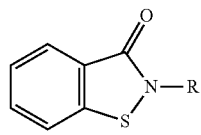

I where R is H or $C_1$-$C_8$ straight or branched chain alkyl comprising the steps of
i) heating a mixture of sodium sulfide hydrate and N-methyl-2-pyrrolidone
ii) distilling from the mixture water and optionally at least a portion of the N-methyl-2-pyrrolidone to leave water-depleted sodium sulfide and optionally water and/or N-methyl-2 pyrrolidone,
iii) reacting at least one benzamide substituted at the 2-position with a leaving group preferably selected from the group consisting of —Cl, —F, —Br, sulfonate such as sulfonic acid, sulfonate ester such as tosyl, mesyl and benzenesulfonyl, —$NO_2$, —CN, carbonyl such as carboxylic acid and ester functionality such as —COOR' where R' is $C_1$-$C_6$ branched or straight chain alkyl, trichloromethyl or trifluoromethyl and —OR" where R" is $C_1$-$C_6$ branched or straight chain alkyl and optionally substituted at the amide functionality by a $C_1$-$C_8$ straight or branched chain alkyl group with the water-depleted sodium sulfide and
iv) subjecting the product to oxidative cyclisation. The oxidative cyclisation can be effected using sulfuryl chloride, hydrogen peroxide or dimethylsulfoxide. In some embodiments the oxidative cyclisation is effected by aqueous hydrogen peroxide. In some embodiments the at least one benzamide is substituted at the 2-position by —Cl. Where the amide functionality is substituted the substituent is preferably is selected from the group consisting of methyl, ethyl, propyl, iso-propyl, butyl, 2-methylpropyl, 1-methylpropyl, t-butyl, pentyl, hexyl, 2-ethylhexyl and octyl. Step iii) can be effected by heating at a temperature in the range 100 to 200° C. for a time in the range 1 to 5 hours. Step i) and ii) can be effected in the presence of toluene or xylene.

2-Mercaptobenzamide is a known material. It is described for example in JP06345723. According to that document 2-mercaptobenzamide can be made by the reaction of 2-halobenzamide with 60% sodium sulfide. The authors of that document contend that when 2-chlorobenzamide is used as the starting material the yield of 2-mercaptobenzamide is 85%. No information of the purity of the 2-mercaptobenzamide is given. The present inventors have repeated the process set forth in Example 1 of JP06345723. The results are set forth herein and show that the yield of pure 2-mercaptobenzamide is low. The purity of the obtained 2-mercaptobenzamide was 56% and the yield based on 2-chlorobenzamide was 43%. The present invention flows from the present inventors' realisation that the large by-product fraction is due to the use of 60% sodium sulfide. The remainder of the crude sodium sulfide is water which hydrolyses the amide functionality of the benzamide.

Commercially available sodium sulfide is available only as the hydrate and contains considerable water. It is not available in industrially useful amounts in anhydrous form. It is possible to produce anhydrous sodium sulphide in the laboratory by reaction of sodium with sulfur in liquid ammonia but this technique is too expensive for industrial scale use.

In accordance with an aspect of the invention in an initial step a sodium sulfide hydrate which is usually obtained in the form of lumps, flakes or powder is slurried with N-methyl-2-pyrrolidone (hereinafter sometimes referred to as "NMP") and heated in a dry atmosphere for example under dry nitrogen until at least some of the water is evaporated optionally with some of the N-methyl-2-pyrrolidone. Typical heating temperatures are between the boiling point of water and the boiling point of N-methyl-2-pyrrolidone at the pressure at which the transformation is taking place. At ambient pressure this implies a temperature in the range of about 100 to about 200° C. preferably the temperature is about 150, 160 or 170 to about 190 or 200° C. The process is not restricted to ambient pressure and other pressures either higher or lower may be used. In preferred embodiments the process is performed at reduced pressure such as 50 to 850 hPa (mbar), in particular from 100 to 400 hPa, preferably from 150 to 350 hPa since less energy is required than at atmospheric pressure. In preferred embodiments of the invention toluene or xylene is also present since this aids water removal using Dean-Stark type apparatus. These materials can also aid in slurrying of the sodium sulfide.

The dried sodium sulfide is then reacted with 2-chlorobenzamide. It is found that much less 2-chlorobenzoic acid is formed compared to when untreated sodium sulfide is used. Additionally next to no starting material remains unreacted. Additionally a small amount of 2,2'-dithiodibenzamide is formed in addition to the 2-mercaptobenzamide. This is not a problem since 2,2'-dithiodibenzamide itself undergoes oxidative cyclization to form BIT. Similar results are obtained using other 2-halobenzamides such a 2-bromobenzamide and especially 2-fluorobenzamide. Other suitable 2-substituted benzamides include those substituted at the 2-position by sulfonate such as sulfonic acid, sulfonate ester such as tosyl, mesyl and benzenesulfonyl —$NO_2$, —CN, carbonyl such as carboxylic acid and ester functionality such as —COOR' where R' is $C_1$-$C_6$ branched or straight chain alkyl, trichloromethyl or trifluoromethyl and —OR" where R" is $C_1$-$C_6$ branched or straight chain alkyl Examples of $C_1$-$C_6$ branched or straight-chain alkyl include methyl, ethyl, propyl, isopropyl, or butyl.

In like manner when it is desired to prepare N-substituted 1,3-benzothiazol-3-one a 2-substituted-N-alkylbenzamide is used. The nature of the alkyl substituent is chosen depending on the structure of the target.

In place of sodium sulfide, other sulfides (SH$^-$) can be used especially those of potassium, lithium and ammonium. These materials are generally anhydrous and so it is not necessary to conduct the drying step.

In principle mercaptobenzamide can be isolated either in free form or as a salt and purified but in practice it is not often necessary to isolate the product in pure form. The 2-mercaptobenzamide or salt thereof can then be oxidatively cyclised for example using hydrogen peroxide to give 1,2-benzisothiazolin-3-one or its salts. Other suitable reagents for oxidative cyclisation may include molecular oxygen for example air, ozone, sodium chlorate (I), sodium perborate, sodium percarbonate, sodium perphosphate, potassium permanganate, ruthenium tetroxide, osmium tetroxide and organic peroxides such as MCPBA, peracetic acid, perbenzoic acid, and perphthalic acid. The preferred oxidative cyclisation reagent is however an aqueous solution of hydrogen peroxide. Preferably the aqueous solution of hydrogen peroxide contains less than about 68 wt % hydrogen peroxide on safety grounds. Suitable concentrations may be in the range of about 3 wt % to about 68 wt % for example about 6 wt % to about 30 wt % such as about 10 to 20 wt % for example about 14 wt %.

In some embodiments the oxidative cyclisation is performed in N-methyl-2-pyrrolidone. Other solvents such as dimethyl sulfoxide, dimethylformamide, dioxane, hexamethylphosphorotriamide, acetonitrile, tetrahydrofuran, water, alcohols such as methanol or ethanol, ketones such as acetone and methyl ethyl ketone, esters such as ethyl acetate, sulfolane, 2-pyrrolidone, 1,2-dimethyl imidazole, 1,3-dimethylimidazolidine, dimethyl sulfone, 1,3-dimethyl-3,4,5,6-tetrahydro-2(1H)-pyrimidone ("DMPU"), dimethylacetamide and acetamide can be used.

The hydrogen peroxide solution may function as a solvent and in some embodiments it is not necessary to add further solvent. Particularly good results are however achieved with dimethyl sulfoxide but N-methyl-2-pyrrolidone also gives good results.

Typically the reaction mixture containing the at least partially dried sodium sulfide is cooled to about 130° C. for example in the range about 120 to about 160° C. and then the substituted benzamide compound such as chlorobenzamide is added. The mixture is then allowed to react. In order to speed the reaction it may be desirable to heat the mixture for example to a temperature in the range about 150 to about 190° C. If wished it is possible to monitor progress of the reaction by for example HPLC. Those skilled will have little difficulty in selecting suitable analytical techniques.

When the reaction is sufficiently advanced the mixture is allowed to cool.

In some embodiments any excess sodium sulfide can be destroyed by adding a mineral acid such as hydrochloric acid and boiling until hydrogen sulfide evolution ceases.

This however is not preferred since the evolved highly toxic hydrogen sulfide has to be disposed of. In preferred embodiments the hydrogen sulfide is destroyed in situ for example by an excess of the oxidizing agent such as hydrogen peroxide, dimethyl sulfoxide and mixtures thereof.

Aqueous hydrogen peroxide is added slowly and once all the peroxide has been added the mixture is worked up by distilling off the water and N-methyl pyrrolidone.

The 1,2-benzisothiazolin-3-one salt can be removed from the reaction mixture for use or can be converted to the 1,2-benzisothiazolin-3-one by reaction with an acid such as hydrochloric acid.

While 2-chlorobenzamide is preferred on cost grounds to produce the 2-mercaptobenzamide it is also possible to use 2-fluorobenzamide, 2-bromobenzamide or other benzamides having an electron withdrawing group at the 2-position such as nitro-, cyano-, sulfonate such as sulfonic acid, sulfonate ester such as tosyl, mesyl and benzenesulfonyl, carbonyl groups such as carboxylic acid and ester functionality such as —COOR' where R' is $C_{1-6}$ branched or straight chain alkyl, trichloromethyl or trifluoromethyl and —OR" where R" is $C_{1-6}$ branched or straight chain alkyl. 2-Fluorobenzamide and 2-chlorobenzamide are especially preferred.

Preferred embodiments of the invention are one-pot reactions in which initially sodium sulfide hydrate is heated with the polar aprotic solvent until sufficient water has been driven off (for example as determined by weight loss) then adding the benzamide and after a further period cooling the mixture and subjecting it to oxidative cyclisation.

Commercial sodium sulfide generally is supplied as the hydrate, $Na_2S.xH_2O$, where the percentage of $Na_2S$ is specified. It is therefore a straightforward matter to calculate how much water is present in the sodium sulfide hydrate. Desirably it is heated with the N-methyl-2-pyrrolidone until much for example at least 50%, more preferably at least 60% such as at least 70% of the water for example at least 80% or at least 90% or even 100% or substantially all of the water is driven off. This can be determined by weighing, by analytical techniques known to the skilled in the art or by spectroscopy. Alternatively the mixture can simply be heated for a period known by experiment or experience to be long enough.

EXAMPLE 1

Comparative

The process for synthesis of 2-mercaptobenzamide, set forth in example 1 of JP 06 345723 was repeated:

15.6 g (0.0983 mol) of 98% 2-chlorobenzamide, 16.0 g (0.1230 mol) of 60% sodium sulfide and 100 g NMP were added to a 200 ml 3 neck flask provided with a stirrer, heated oil bath thermometer and condenser. The mixture was stirred at 160° C. for 4 hours.

NMP was distilled off at reduced pressure and the residue dissolved in 100 g of water.

The mixture was acidified to pH 4.0 by adding 35% hydrochloric acid at 20° C.

The separated crystalline material was isolated by filtration, washed with water and dried to constant weight of 11.6 g at 40° C.

HPLC analysis, calibrated by authentic samples, revealed the following composition of the isolated product:

(g; mol; molar % of theory): (1.2; 0.0071; 7.2) 2-chlorobenzamide, (2.8; 0.0177; 18.0) 2-chlorobenzoic acid and (6.5; 0.0424; 43.2) 2-mercaptobenzamide.

Based on weight the purity of 2-mercaptobenzamide is 56.0%.

EXAMPLE 2

23.4 g (0.18 mol) of 60% sodium sulfide (40% water) and 160 g N-methyl-2-pyrrolidone (NMP) was added to a 500 ml 3 neck flask provided with a heated oil bath, stirrer and a thermometer. The mixture was stirred at 190° C. and purged with nitrogen to a weight loss of 25 g. To the dried slurry of sodium sulfide at 130° C., 18.1 g (0.1163 mol), 2-chlorobenzamide of 98% purity was added and the mixture heated to 175° C. for 4 hours. HPLC analysis of the reaction mixture, calibrated with authentic samples showed (g; mol; molar % of theory): (0.37; 0.0012; 2) 2,2'-dithiodibenzoic acid and (16.5; 0.108; 88) 2-mercaptobenzamide. 2-chlorobenzoic acid was not detected.

The mixture was cooled to 70° C., 40 g of water was added and pH adjusted to 4.0, by adding 28.5 g of 35% hydrochloric acid. The mixture was heated to boiling until hydrogen sulfide evolution ceased. Evolved hydrogen sulfide was absorbed for disposal in a caustic solution. At 20° C., caustic solution (such as alkali hydroxide or carbonates or other salts or other bases) was added to the reaction mixture to bring the pH back to 9 or above and 27.0 g (0.111 mol) 14% hydrogen peroxide was introduced over 30 min.

Water and NMP was distilled off at reduced pressure and the residue was dispersed in 125 g of water. The mixture was adjusted to pH 5 with 35% hydrochloric acid. Separated BIT crystals were filtered off, washed with water and air dried to constant weight. BIT yield 14.3 g (0.094 mol) which is 80.8% of theory. Purity 99.5% by HPLC. The NMP can be recovered for reuse by known methods.

EXAMPLE 3

23.4 g (0.12 mol) of 60% sodium sulfide (40% water) and 160 g N-methyl-2-pyrrolidone (NMP) was added to a 500 ml 3 neck flask provided with a heated oil bath, stirrer and a thermometer. The mixture was stirred at 190° C. and purged with nitrogen to a weight loss of 25 g. To the dried slurry of sodium sulfide at 130° C., 18.1 g (0.117 mol), 2-chlorobenzamide was added and the mixture heated to 175° C. for 4 hours. HPLC analysis of the reaction mixture, calibrated with authentic samples showed (g; mol; molar % of theory): (0.37; 0.0012; 2) 2,2'-dithiodibenzoic acid and (16.5; 0.108; 88) 2-mercaptobenzamide. 2-chlorobenzoic acid was not detected. NMP was distilled off at reduced pressure.

The mixture was cooled to 70° C., 125 g of water was added and pH adjusted to 3.0, by adding 28.5 g of 35% hydrochloric acid. The mixture was heated to boiling until hydrogen sulfide evolution ceased. Instead of boiling hydrogen sulfide evolution could be promoted by a gas stream. Evolved hydrogen sulfide can be absorbed in a caustic solution for disposal. At 20° C., caustic solution (such as alkali hydroxide or carbonate or other salts or other bases) is added to the reaction mixture to bring the pH back to 9 or above. 27.0 g (0.111 mol) 14% hydrogen peroxide was introduced over 30 min.

The mixture was acidified to pH 5 with 35% hydrochloric acid and the BIT crystals filtered off, washed with water and air dried to constant weight. The yield and quality of BIT was the same as in Example 2.

EXAMPLE 4

23.4 g (0.12 mol) of 60% sodium sulfide (40% water) and 160 g N-methyl-2-pyrollidone (NMP) was added to a 500 ml 3 neck flask provided with a heated oil bath, stirrer and a thermometer. The mixture was stirred at 130° C. and water followed by water/NMP, then NMP is distilled off under vacuum until about 10 wt % of the total reaction mixture was distilled off. The oil bath temperature was adjusted to maintain distillation. The reaction mixture was cooled down to 130° C. To the dried slurry of sodium sulfide at 130° C., 18.1 g (0.117 mol), 2-chlorobenzamide (which can be dissolved in NMP or other inert organic solvent such as aprotic polar solvent) was added and the mixture heated to 175° C. for 4 hours under nitrogen. HPLC analysis of the reaction mixture, calibrated with authentic samples showed completion of reaction (<0.5% of starting material. 2-Chlorobenzoic acid was not detected.)

At 20° C., caustic solution (such as alkali hydroxide or salts such as carbonates or other bases) was added to the reaction mixture to bring the pH to 9 or above. 27.0 g (0.111 mol) 14% hydrogen peroxide was introduced over 30 min and the mixture stirred until completion of reaction. If necessary more hydrogen peroxide was added. The solvents (water and NMP) were distilled off under vacuum and the residue is taken back in water. The aqueous mixture was acidified to pH 4 with 35% hydrochloric acid and the BIT crystals were filtered off, washed with water and air dried to constant weight. The yield and quality of the BIT was the same as in Example 2.

EXAMPLE 5

Example 4 was repeated up to the point where the reaction of 2-chlorobenzamide with sodium sulfide was complete.

The solvent (NMP) was distilled off under vacuum and the residue taken back in water.

At 20° C., caustic solution (such as alkali hydroxide or carbonate or other salts or other bases) was added to the reaction mixture to bring the pH to 9 or above. 27.0 g (0.111 mol) 14% hydrogen peroxide was introduced over 30 min. The reaction mixture was stirred until completion of reaction if necessary with the addition of further hydrogen peroxide. The aqueous solution was acidified to pH 5 with 35% hydrochloric acid and BIT crystals filtered off, washed with water and air dried to constant weight. The yield and quality of BIT was the same as in Example 2.

EXAMPLE 6

Example 4 was repeated until the reaction of 2-chlorobenzamide with sodium sulfide was complete.

The solvent (NMP) was distilled off under vacuum and the residue treated with DMSO.

At 20° C., potassium carbonate (or alkali hydroxide or other base) was added to the reaction mixture to bring the pH to 9 or above. 27.0 g (0.111 mol) 14% hydrogen peroxide was introduced over 30 min and the mixture stirred until reaction was complete. If necessary more hydrogen peroxide was added. DMSO was distilled off under vacuum and the residue was stirred with toluene for 30 minutes. The solid was decanted and rinsed with toluene. It was then treated with water and then acidified to pH 5 with 35% hydrochloric acid. BIT crystals were filtered off, washed with water and air dried to constant weight. The yield and quality was the same as in Example 2

EXAMPLE 7

Example 4 was repeated until the reaction of 2-chlorobenzamide with sodium sulfide was complete save that 7.4 g (0.0569 mol) of 60% sodium sulfide (40% water), 133 g (NMP) and 6.0 g (0.03856 mol), 2-chlorobenzamide were employed.

NMP was distilled off under vacuum and the residue was taken back in water.

The reaction mixture was acidified to pH 6.0 with concentrated HCl, and then potassium carbonate powder was added to bring the pH to 10.5. Hydrogen peroxide was added to the reaction mixture. The ensuing reaction was followed by HPLC sampling and once substantially complete the reaction mixture was acidified to pH 4.5 at temperature <10° C. resulting in precipitation of BIT. The reaction mixture was stirred for at least 1 hour at <10° C., then the BIT was filtered under vacuum. The cake was washed with water and dried. Yield 80% purity 97%.

EXAMPLE 8

Example 4 was repeated save that in place of 2-chlorobenzamide 16.3 g (0.117 mol), 2-fluorobenzamide was used. The reaction was substantially faster than when 2-chlorobenzamide was used and was complete in 65 minutes at 170° C. as compared with 240 minutes at 175° C. when 2-chlorobenzamide was used.

EXAMPLE 9

Preparation of 2-methyl-1,2-benzisothiazolin-3-one 50 g N-methyl-2-pyrrolidone (NMP) was added to a 100 ml 3 neck flask provided with a heated oil bath, stirrer and thermometer. 6.6 g (0.0507 mol) of 60% sodium sulfide (40% water), 7.0 g of water and 19.3 g of xylene was added to the reaction flask. At a bath temperature of 150° C. water and xylene was distilled off into a Dean and Stark receiver. The bath temperature was raised further to 220° C. to distil off remains of xylene. To the dried slurry of sodium disulfide in NMP, a solution of 6.0 g (0.0347 mol) 2-chloro-N-methylbenzamide in 12 g NMP was added with stirring at 175° C. over 20 min. and the reaction continued for a further 2.5 hrs. The mixture was cooled to 30° C. The pH is adjusted to 4.0 with 35% hydrochloric acid and the mixture is heated to 120° C. for a short while to expel hydrogen sulfide and water. To the stirred reaction mixture at 25° C. 4.7 g (0.0347 mol) of sulfuryl chloride was added over 15 min and stirring was continued for a further 60 min. HPLC analysis showed a conversion of 2-chloro-N-methylbenzamide to 2-methyl-1,2-benzisothiazolin-3-one of 74.1 molar %.

EXAMPLE 10

Preparation of 2-methyl-1,2-benzothiazolin-3-one

A mixture of sodium sulfide (~60%, 19.8 g, 0.152 mol), xylene (49 g), water (18.9 g) and NMP (160.3 g) in a reaction flask equipped with condenser and Dean-Stark trap was heated to reflux. After removal of water the xylene was distilled off by increasing the oil bath temp to 220° C. The mixture was allowed to cool to 175° C. and a solution of 2-chloro-N-methylbenzamide (18.0 g, 0.105 mol) in NMP (40.7 g) added dropwise. The mixture was heated at 175° C. for 4 hours.

The mixture was concentrated in vacuo to one third volume and allowed to cool to 40° C. Water (75 g) was added and the pH adjusted to 4 by addition of 35% hydrochloric acid (24.3 g). The mixture was heated to 90° C. with nitrogen sparging for 60 minutes to expel residual hydrogen sulphide to afford a suspension of a sand coloured solid and brown supernatant solution (total weight=135.3 g). A 7.3 g portion of the above suspension was stirred at room temperature and diluted with water (5 ml) and acetonitrile (10 ml) and treated with sodium hydrogen carbonate (1.0 g, 12.0 mmol) and hydrogen peroxide (33% aq solution, 0.95 ml, 1.04 g, 10.5 mmol, added in 4 portions over a 4 hour period). HPLC analysis showed 2-methyl-1,2-benzothiazolin-3-one as the main reaction component in 58.1 mol % yield.

EXAMPLE 11

Preparation of 2-butyl-1,2-benzothiazolin-3-one

A mixture of sodium sulfide (~60%, 9.9 g, 0.076 mol), xylene (25.7 g), water (9.8 g) and NMP (79.7 g) in a reaction flask equipped with condenser and Dean-Stark trap was heated to reflux. After removal of water the xylene was distilled off by increasing the oil bath temp to 220° C. The mixture was allowed to cool to 175° C. and a solution of 2-chloro-N-butylbenzamide (11.1 g, 0.052 mol) in NMP (20 g) added dropwise. The mixture was heated at 175° C. for 4 hours. The mixture allowed to cool to 40° C. and 35% hydrochloric acid (13.7 g) was added until the pH was adjusted to 4. The mixture was heated to 90° C. with nitrogen sparging for 20 minutes and then the temperature was raised to 130° C. for a further 60 min to expel residual hydrogen sulfide and water to leave a suspension of a sand coloured solid and reddish brown supernatant solution (total weight=95.6 g). An 8.85 g portion of the above suspension was treated with sulfuryl chloride (0.3 ml, 0.5 g, 3.70 mmol), added in four aliquots with 20min between additions. HPLC analysis showed 2-butyl-1,2-benzothiazolin-3-one as the main reaction component in 74.1 mol % yield.

EXAMPLE 12

Preparation of 2-butyl-1,2-benzothiazolin-3-one

A mixture of sodium sulfide (~60%, 9.9 g, 0.076 mol), xylene (25.7 g), water (9.8 g) and NMP (79.7 g) in a reaction flask equipped with condenser and Dean-Stark trap was heated to reflux. After removal of water the xylene was distilled off by increasing oil bath temp to 220° C. The mixture was allowed to cool to 175° C. and a solution of 2-chloro-N-butylbenzamide (11.1 g, 0.052 mol) in NMP (20 g) added dropwise. The mixture was heated at 175° C. for 4 hours. The mixture was allowed to cool to 40° C. and 35% hydrochloric acid (13.7 g) was added until the pH was adjusted to 4. The mixture was heated to 90° C. with nitrogen sparging for 20 minutes and then the temperature was raised to 130° C. for a further 60 min to expel residual hydrogen sulfide and water to leave a suspension of a sand coloured solid and reddish brown supernatant solution (total weight=95.6 g). An 8.85 g portion of the above suspension was stirred at room temperature and diluted with water (10 ml) and acetonitrile (5 ml) and treated with sodium hydrogen carbonate (0.60 g, 7.2 mmol) and hydrogen peroxide (33% aq solution, 0.73 ml, 0.80 g, 7.96 mmol, added in 5 portions). HPLC analysis showed 2-butyl-1,2-benzothiazolin-3-one as the main reaction component in 41 mol % yield.

The invention claimed is:
1. A process for preparing a compound of Formula I

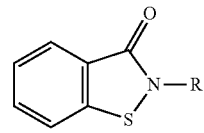

where R is $C_1$-$C_8$ straight or branched chain alkyl,
said process comprising the steps of
i) heating a mixture of sodium sulfide hydrate and N-methyl-2-pyrrolidone ii) distilling from said mixture water and optionally at least a portion of said N-methyl-2-pyrrolidone to leave water-depleted sodium sulfide and optionally water and/or N-methyl-2-pyrrolidone, iii) reacting with the water-depleted sodium sulfide at least one benzamide substituted at the 2-position with a group selected from the group consisting of —Cl, —Br, —F, —NO$_2$, —CN, sulfonate, sulfonate ester such as tosyl, mesyl and benzenesulfonyl, carbonyl groups such as carboxylic acid and ester functionality such as —COOR' where R' is C$_{1-6}$ branched or straight chain alkyl, trichloromethyl or trifluoromethyl and —OR" where R" is C$_{1-6}$ branched or straight chain alkyl and substituted at the amide functionality by a group consisting of methyl, ethyl, propyl, iso-propyl, butyl, 2-methylpropyl, 1-methylpropyl, t-butyl, pentyl, hexyl, 2-ethylhexyl and octyl, and iv) subjecting the product of step iii) to oxidative cyclisation.

2. The process as claimed in claim 1 wherein the oxidative cyclisation is effected by a reagent selected from sulfuryl chloride, hydrogen peroxide or dimethylsulfoxide.

3. The process as claimed in claim 2 wherein the oxidative cyclisation is effected by aqueous hydrogen peroxide.

4. The process as claimed in claim 1 wherein the at least one benzamide is substituted at the 2-position by Cl.

5. The process as claimed in claim 1 wherein step iii) is effected by heating at a temperature in the range 100 to 200° C. for a time in the range 1 to 5 hours.

6. The process as claimed in claim 1, wherein step i) and ii) are effected in the presence of toluene or xylene.

\* \* \* \* \*